United States Patent [19]

Sheldon et al.

[11] 4,110,361

[45] Aug. 29, 1978

[54] PREPARATION OF ESTERS

[75] Inventors: Roger A. Sheldon; Peter Been, both of Amsterdam, Netherlands

[73] Assignee: Shell Oil Company, Houston, Tex.

[21] Appl. No.: 765,185

[22] Filed: Feb. 3, 1977

[30] Foreign Application Priority Data

Mar. 1, 1976 [GB] United Kingdom ................. 8045/76
Mar. 1, 1976 [GB] United Kingdom ................. 8046/76

[51] Int. Cl.$^2$ .................. C07C 120/00; C07C 121/66
[52] U.S. Cl. ............................................... 260/465 D
[58] Field of Search ................................... 260/465 D

[56] References Cited

U.S. PATENT DOCUMENTS 3,835,176  9/1974  Matsuo et al. .................... 260/465 D

OTHER PUBLICATIONS

Zymalkowski et al., Arch. pharmaz. Ber. pharmaz. Ges. 62, Nr. 5, pp. 218-224 (1956).
Francis et al., J. Chem. Soc., 95, pp. 1403-1409 (1909).
Kinder et al., Arch. Pharm., 271, pp. 431-439 (1933).
Coronyn, J. Org. Chem., 14, pp. 1013-1022 (1949).
Fisher et al., J. Org. Chem., 24, pp. 1650-1654 (1959).

*Primary Examiner*—Dolph H. Torrence

[57] ABSTRACT

Certain carboxylic acid esters also containing a cyano group are prepared by reacting an acid halide, an aldehyde and a water-soluble cyanide in the presence of a water-immiscible aprotic solvent and surface-active agent as catalyst.

30 Claims, No Drawings

PREPARATION OF ESTERS

BACKGROUND OF THE INVENTION

1. Field of the Invention

The invention relates to a process for the preparation of certain cyano-substituted-carboxylic acid esters by reacting an acid halide, an aldehyde and a water-soluble cyanide.

2. Description of the Prior Art

According to U.S. Pat. No. 3,835,176, addition of substituted cyclopropanecarbonyl halides and m-substituted benzaldehydes, if necessary dissolved in an aprotic solvent, to an aqueous solution of sodium cyanide or potassium cyanide and stirring of the mixture obtained until no more conversion takes place, affords the desired esters. The experiment described in Example 4 of the above U.S. patent was conducted in the absence of a solvent, with an unsaturated aqueous solution of sodium cyanide, with a 20% molar excess of the cyclopropanecarbonyl halide (calculated on aldehyde) and at a temperature of 0° C.

Such a process has the disadvantages that the yield of the ester is relatively low and that keeping the temperature at 0° C and using the said molar excess are expensive.

The present invention obviates these disadvantages.

SUMMARY OF THE INVENTION

The present invention is directed to a process for the preparation of an ester of formula I

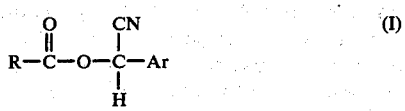

wherein Ar is an optionally substituted aromatic group and R is an optionally substituted acyclic or saturated cyclic hydrocarbyl group, by contacting an aromatic aldehyde of the formula ArC(O)H and an acyl halide of the formula RC(O)Hal, in which formulas Ar and R have the same meanings as in formula I and Hal is a halogen atom having an atomic number of from 9 to 53, inclusive, with water, a water-soluble cyanide, a substantially water-immiscible aprotic solvent and a surface-active agent as phase-transfer catalyst.

A "surface-active agent" is defined as in Kirk-Othmer, "Encyclopedia of Chemical Technology", second edition, volume 19(1969), page 508: "An organic compound that encompasses in the same molecule two dissimilar structural groups, one being water-soluble and one being water-insoluble".

The surface-active agent is preferably non-ionic. Non-ionic synthetic surface-active agents may be broadly defined as compounds aliphatic or alkylaromatic in nature which do not ionize in water solution. For example, a well known class of non-ionic agents is made available on the market under the trade name of "Pluronic." These compounds are formed by condensing ethylene oxide with an hydrophobic base formed by the condensation of propylene oxide with propylene glycol. The hydrophobic portion of the molecule which, of course, exhibits water insolubility has a molecular weight of from about 1,500 to 1,800. The addition of polyoxyethylene radicals to this hydrophobic portion tends to increase the water solubility of the molecule as a whole and the liquid character of the product is retained up to the point where polyoxyethylene content is about 50% of the total weight of the condensation product.

Other suitable nonionic agents include: (1) The polyethylene oxide condensates of alkyl phenols, e.g., the condensation products of alkyl phenols having an alkyl group containing from about 6 to 12 carbon atoms in either a straight chain or branched chain configuration, with ethylene oxide, the said ethylene oxide being present in amounts equal to 10 to 25 moles of ethylene oxide per mole of alkyl phenol. The alkyl substituent in such compounds may be derived from polymerized propylene, diisobutylene, octene, or nonene, for example. (2) Those derived from the condensation of ethylene oxide with the product resulting from the reaction of propylene oxide and ethylenediamine. For example, compounds containing from about 40% to about 80% polyoxyethylene by weight and having a molecular weight of from about 5,000 to about 11,000 resulting from the reaction of ethylene oxide groups with a hydrophobic base constituted of the reaction product of ethylene diamine and excess propylene oxide, said hydrophobic base having a molecular weight of the order of 2,500 to 3,000, are satisfactory. (3) The condensation product of aliphatic alcohols having from 8 to 18 carbon atoms, in either straight chain or branched chain configuration, with ethylene oxide, e.g., a coconut alcohol-ethylene oxide condensate having from 10 to 30 moles of ethylene oxide per mole of coconut alcohol, the coconut alcohol fraction having from 10 to 14 carbon atoms. (4) Long chain tertiary amine oxides corresponding to the following general formula, $R_1R_2R_3N \rightarrow O$, wherein $R_1$ is an alkyl radical of from about 8 to 18 carbon atoms, and $R_2$ and $R_3$ are each methyl or ethyl radicals. The arrow in the formula is a conventional representation of a semi-polar bond. Examples of amine oxides suitable for use in this invention include dimethyldodecylamine oxide, dimethyloctylamine oxide, dimethyldecylamine oxide, dimethyltetradecylamine oxide, dimethylhexadecylamine oxide. (5) Long chain tertiary phosphine oxides corresponding to the following formula $RR'R''P \rightarrow O$, wherein R is an alkyl, alkenyl or monohydroxyalkyl radical ranging from 10 to 18 carbon atoms in chain length and R' and R'' are each alkyl or monohydroxyalkyl groups containing from 1 to 3 carbon atoms. The arrow in the formula is a conventional representation of a semi-polar bond. Examples of suitable phosphine oxides are:
dimethyldodecylphosphine oxide,
dimethyltetradecylphosphine oxide,
ethylmethyltetradecylphosphine oxide,
cetyldimethylphosphine oxide,
dimethylstearylphosphine oxide,
cetylethylpropylphosphine oxide,
diethyldodecylphosphine oxide,
diethyltetradecylphosphine oxide,
bis(hydroxymethyl)dodecylphosphine oxide,
bis(2-hydroxyethyl)dodecylphosphine oxide,
2-hydroxypropylmethyltetradecylphosphine oxide,
dimethyloleylphosphine oxide, and
dimethyl-2-hydroxydodecylphosphine oxide.

(6) Dialkyl sulfoxides corresponding to the following formula, $RR'S \rightarrow O$, wherein R is an alkyl, alkenyl, beta- or gamma-monohydroxyalkyl radical or an alkyl or beta- or gamma-monohydroxyalkyl radical containing one or two other oxygen atoms in the chain, the R groups ranging from 10 to 18 carbon atoms in chain length, and wherein R' is methyl or ethyl. Examples of suitable sulfoxide compounds are:
dodecylmethyl sulfoxide
tetradecylmethyl sulfoxide
3-hydroxytridecylmethyl sulfoxide
2-hydroxydodecylmethyl sulfoxide
3-hydroxy-4-decoxybutylmethyl sulfoxide
3-hydroxy-4-dodecoxybutylmethyl sulfoxide
2-hydroxy-3-decoxypropylmethyl sulfoxide
2-hydroxy-3-dodecoxypropylmethyl sulfoxide
dodecylethyl sulfoxide
2-hydroxydodecylethyl sulfoxide (7) The ammonia, monoethanol and diethanol amides of fatty acids having an acyl moiety of from about 8 to about 18 carbon atoms;

(8) A sorbitan monoester with a long chain fatty acid of 8 to 20 carbon atoms; or (9) An alkylbenzene containing a straight-chain alkyl group. Suitable alkylbenzenes contain an alkyl group of 8 to 20 carbon atoms.

Preferred surface-active agents are poly(alkyleneoxy) derivatives formed by reacting a higher alcohol, alkylphenol or fatty acid with ethylene oxide or propylene oxide. Suitable alcohols, alkylphenols or fatty acids contain an alkyl group of from 8 to 20 carbon atoms and the number of alkyleneoxy units is in the range of 1 to 50. It is preferable to use an alcohol ethoxylate such as the ethoxylates derived by ethoxylation of primary or secondary, straight-chain or branched alcohols. A single alcohol may be used e.g., octyl alcohol, decyl alcohol, dodecyl alcohol, but preferably a mixture of alcohols is used. The mixture of alcohols may contain small amounts of alcohols below $C_7$ and above $C_{13}$ but at least 90%w, and preferably at least 95%w, of the alcohols thereof are in the $C_9$ to $C_{13}$ range. Preferred mixtures of alcohols are those mixtures of $C_9$ to $C_{11}$ alcohols such as those prepared by hydroformylation of olefins. The amount of ethylene oxide used to prepare such ethoxylates is suitably such so as to provide an average from 1 to 13 moles, and preferably 5 to 9 moles, of ethylene oxide per mole of alcohol (or alcohol mixture). Examples of such ethoxylates are "Dobanol$_{45-11}$" formed from a $C_{14}$ to $C_{15}$ straight-chain alcohol mixture and containing an average of eleven ethyleneoxy units or preferably "Dobanol$_{91-6}$" formed from a $C_9$ to $C_{11}$ straight-chain alcohol mixture with an average of six ethyleneoxy units (both trade names are registered trade marks).

The molar ratio of the amount of phase transfer catalyst to the amount of aromatic aldehyde of the formula ArC(O)H may vary within wide limits, but is suitably from 1:5 to 1:500. The use of low molar ratios will require a longer time to complete the reaction, whilst the use of higher molar ratios naturally increases the cost to produce a given quantity of ester. Thus, the choice of reaction time and molar ratio catalyst to aromatic aldehyde are mutually interdependant, and in any individual instance will depend on the local economic factors. Very good results are usually obtained at molar ratios from 1:10 to 1:100.

Another advantage of the process according to the present invention is that the molar ratio of the amount of (cyclo)aliphatic acyl halide to the amount of aromatic aldehyde can be kept so low that a molar excess of the halide is not or hardly not required. This molar ratio is preferably in the range of from 1.1 to 1.0. When the substantially water-immiscible aprotic solvent is a (cyclo)alkane or a mixture of (cyclo)alkanes molar ratios equal to 1.0 give excellent results.

The molar ratio of the amount of water-soluble cyanide to the amount of aromatic aldehyde is suitably from 1.5 to 1.00 and preferably from 1.3 to 1.02. By "water-soluble cyanide" is meant a water-soluble salt of hydrogen cyanide. Of the water-soluble cyanides alkalimetal cyanides and alkaline-earth-metal cyanides are preferred. Sodium cyanide is particularly preferred, because it affords the esters of the formula I in the shortest reaction time.

The temperature at which the process is conducted is suitably above 0° C and is preferably in the range of from 10° C to 50° C. Very good results have been obtained at temperatures in the range of from 15° C to 40° C. The process has the advantage that ambient temperatures are very suitable.

The most suitable substantially water-immiscible aprotic solvent is a (cyclo)alkane or a mixture of (cyclo)alkanes, because they allow the shortest reaction times. The use of these solvents is claimed in our concurrently filed U.S. application U.S. Ser. No. 765,188, filed Feb. 3, 1977. Examples of suitable (cyclo)alkanes are those having up to 10 carbon atoms, preferably 6 to 10 carbon atoms, e.g., n-hexane, n-heptane, n-octane, n-nonane, n-decane and their isomers (for example 2-methylpentane, 3-methylpentane, 2-methylhexane, 3-methylhexane and 2,4,4-trimethylpentane) and cyclohexane and methylcyclohexane. Gasolines rich in alkanes are also very suitable, for example with a boiling range at atmospheric pressure between 40° and 65° C, 60° and 80° C or 80° and 110° C. Very good results have been obtained with n-heptane and cyclohexane.

Other very suitable substantially water-immiscible aprotic solvents are aromatic hydrocarbons and chlorinated hydrocarbons, for example benzene, toluene, p-, m- and p-xylene, the trimethylbenzenes, dichloromethane, 1,2-dichloromethane, chloroform, monochlorobenzene and 1,2- and 1,3-dichlorobenzene. Very good results have been obtained with toluene.

The process according to the present invention may be conducted starting from unsaturated or saturated aqueous solutions of water-soluble cyanide and in the latter case in the presence or absence of solid water-soluble cyanide. The use of solid water-soluble cyanide is covered in our concurrently filed U.S. patent application Ser. No. 765,184, filed Feb. 3, 1977.

It has been found that when in a given case in which in successive comparable experiments less water and more solid water-soluble cyanide are applied (starting from a saturated aqueous solution of cyanide containing no solid water-soluble cyanide and keeping the total amount of water-soluble cyanide constant) the reaction time can be kept shorter and shorter, passes a minimum and then becomes longer and longer until it has become as long as in the starting case.

The use of (cyclo)alkanes in combination with aqueous solution of cyanide in the absence of solid water-soluble cyanide allows very short reaction times. The use of aromatic hydrocarbons or chlorinated hydrocarbons in combination with aqueous solutions of cyanide in the absence of solid water-soluble cyanide needs longer reaction times, but the use of these two groups of solvents in combination with solid water-soluble cyanide allows very short reaction times. Solid water-soluble cyanide may also be used in the presence of (cyclo)alkanes, but the reaction times can already be kept very short in the absence of the former. The above-mentioned minimum reaction time is usually obtained when molar ratios of the amount of water to the total amount of water-soluble cyanide is higher than 0.05 and particularly in the range of from 0.05 to 1. For comparison it may be stated that the molar ratios of water to sodium cyanide in a saturated aqueous solution of sodium cyanide at 10° C and 35° C are 5.7 and 3.3, respectively. Consequently, extremely small amounts of water are sufficient to obtain the shortest reaction times. Furthermore, the yield of the ester of the formula I is usually very high and sometimes quantitative. In addition to the possibility of using short reaction times the use of solid water-soluble cyanide has a cost-saving effect, since smaller volumes of water can be handled.

Other examples of substantially water-immiscible aprotic solvents are dialkyl ethers and substantially water-immiscible alkanones, for example diethyl ether, diisopropyl ether and diisobutyl ketone. For these solvents the above-mentioned minimum reaction time can easily be determined by means of simple experiments in which the molar ratio of the amount of water to the total amount of water-soluble cyanide is varied. Mixtures of solvents, for example of alkanes and aromatic hydrocarbons may be applied, for example of n-heptane containing up to 10% by weight of benzene and/or toluene.

The optionally substituted aromatic group Ar in the aromatic aldehyde of the formula ArC(O)H may be carbocyclic or heterocyclic. Examples of carbocyclic groups are phenyl, 1-naphthyl, 2-naphthyl and 2-anthryl groups. Heterocyclic aromatic groups are derived from hetero-aromatic compounds which are defined as in Kirk-Othmer, "Encyclopedia of Chemical Technology", Second Edition, Volume 2 (1963), page 702: obtained by replacement of one or more carbon atoms of a carbocyclic aromatic compound by a hetero-atom - for example pyridine, pyrimidine, pyrazine, quinoline and isoquinoline - and also include those heterocyclic compounds having five-membered rings which show aromatic characteristics and are mentioned on page 703 of said volume, for example thiophene, pyrrole, furan, indole and benzothiophene. As an aromatic group an optionally substituted phenyl group is very suitable. Examples of substituents are hydrocarbyl and hydrocarbyloxy groups. Very good results have been obtained with phenoxybenzaldehydes, particularly m-phenoxybenzaldehyde.

The group R in the formula RC(O)Hal may, for example, be an optionally substituted alkyl group. The alkyl group may be straight or branched. The alkyl groups preferably have a tertiary or quaternary carbon atom bound to the group -C(O)Hal. Examples of such alkanoyl halides are 2-methyl-propanoyl chloride, 2,2-dimethylpropanoyl chloride and 2-methylbutanoyl bromide. Very good results have been obtained with 2-methylpropanoyl chloride. The alkyl group may carry as substituents, for example, hydrocarbyloxy or substituted phenyl groups, such as halophenyl or alkylphenyl. Very good results have been obtained with 1-(4-chlorophenyl)-2-methylpropyl groups. The expression "saturated cyclic hydrocarbyl group" in this patent application refers to cyclic hydrocarbyl groups in which the ring is saturated; this ring may carry substituents for example alkyl groups of 1 to 6 carbon atoms such as methyl, halogen atoms having atomic numbers of 9 to 35, inclusive, such as chlorine, bromine or fluorine or unsaturated side chains such as isobutenyl, dichlorovinyl or dibromovinyl. Examples of saturated cyclic hydrocarbyl groups are cyclopropyl, cyclobutyl and cyclohexyl groups. Very good results have been obtained with optionally substituted cyclopropanecarbonyl halides, particularly with 2,2,3,3-tetramethylcyclopropanecarbonyl halides and 2-(2,2-dichlorovinyl)-3,3-dimethylcyclopropanecarbonyl halides. The later halides may have a cis or trans structure or may be a mixture of such structures and may be a pure optical isomer or a mixture of optical isomers.

The atom Hal in the formula RC(O)Hal is preferably a chlorine or bromine atom and in particular a chlorine atom.

The process according to the invention may be carried out by gradual addition of the acyl halide to a vigorously agitated, e.g. stirred, mixture of the other starting compounds (particularly recommended when R in the formula RC(O)Hal represents a 2,2,3,3-tetramethylcyclopropyl group) and often by placing together the total amounts of the starting compounds and vigorous agitating, e.g. stirring, of the mixture thus formed, which is particularly recommended when R represents a 1-(4-chlorophenyl)-2-methylpropyl, an isopropyl or a 2-(2,2-dichlorovinyl)-3,3-dimethylcyclopropyl group.

The process is of particular interest to prepare pesticidally active esters, for example when the aromatic aldehyde is 3-phenoxybenzaldehyde and the acyl halide is an aralkyl halide such as 2-(4-chlorophenyl)-3-methylbutanoyl chloride, or a substituted-cyclopropanecarbonyl halide such as 2,2,3,3-tetramethylcyclopropanecarbonyl chloride or 2-(2,2-dichlorovinyl)-3,3-dimethylcyclopropanecarbonyl chloride, because the esters then formed are α-cyano-3-phenoxybenzyl 2-(4-chlorophenyl)-3-methylbutanoate, α-cyano-3-phenoxybenzyl 2,2,3,3-tetramethylcyclopropanecarboxylate and α-cyano-3-phenoxybenzyl 2-(2,2-dichlorovinyl)-3,3-dimethylcyclopropanecarboxylate, respectively, all of which are pesticidally active compounds disclosed in Belgian patent 801,946, U.S. Pat. No. 3,835,176 and Netherlands publication No. 7,307,130, respectively.

EXAMPLES

The Examples further illustrate the invention. All experiments were conducted at a temperature of 23° C. The sodium cyanide used consisted of particles having a largest dimension of 0.5 mm and contained 0.44% by weight of water. The molar ratio of water to sodium cyanide has been calculated taking into account the water present in the sodium cyanide and the water added, if any. For comparison it may be stated that the molar ratio of water to sodium cyanide in a saturated aqueous solution of sodium cyanide having a temperature of 23° C is 4.1. The reaction mixtures were stirred vigorously and analysed by gas-liquid chromatography to determine the yield of the ester formed. Reaction mixtures were filtered to remove precipitated sodium chloride and solid sodium cyanide, if any, and drying of solutions was carried out over anhydrous sodium sulphate. Flashing of the solvent took place in a film evaporator at a pressure of 15 mm Hg. All yields are calculated on starting aromatic aldehyde.

EXAMPLE I

Preparation of α-cyano-3-phenoxybenzyl 2-(2,2-dichlorovinyl)-3,3-dimethylcyclopropanecarboxylate in the presence of n-heptane A 50 ml round-bottomed flask equipped with a magnetic stirrer was charged with 10 mmol of 3-phenoxybenzaldehyde, an amount of 2-(2,2-dichlorovinyl)-3,3-dimethylcyclopropanecarbonyl chloride, 12 mmol of sodium cyanide, water, a catalyst, if any and 20 ml of n-heptane. The mixture thus formed was stirred. Two experiments were carried out in this manner, see Table I. Column 3, 4 and 5 state the amounts of catalyst, water and acyl chloride added. The sodium cyanide was completely dissolved. The yield of the desired ester is presented in column 7.

TABLE I

| 1 | 2 | 3 | 4 | 5 | 6 | 7 |
|---|---|---|---|---|---|---|
| | Catalyst | | | Acyl | | |
| Exp. no. | name | amount %mol on aldehyde | Water added ml | chloride, mmol | Reaction time, h | Yield of ester, % |
| 1[1] | — | — | 1.0 | 10.2 | 3 | 49 |
| | | | | | 21 | 94 |
| | | | | | 44 | 99 |
| 2 | Dobanol 91-6[2] | 2 | 1.0 | 10.0 | 1 | 62 |
| | | | | | 2 | 80 |
| | | | | | 18 | 99 |

[1] not according to the invention
[2] a registered trade name for a non-ionic surface-active agent formed from a $C_9$-$C_{11}$ alcohol mixture and containing an average of 6 ethyleneoxy units; the alcohol mixture consists of 85% n-alkanols and 15% 2-alkylakanols.

EXAMPLE II

Preparation of α-cyano-3-phenoxybenzyl 2-(4-chlorophenyl)-3-methylbutanoate in the presence of toluene A 50 ml roundbottomed flask equipped with a magnetic stirrer was charged with 10 mmol of 3-phenoxybenzaldehyde, 10.5 mmol of 2-(4-chlorophenyl)-3-methylbutanoyl chloride, 12, mmol of sodium cyanide and 20 ml of toluene. The mixture thus formed was stirred. The yields of the desired ester after 3 and 20 hours' stirring are presented in Table II, see experiment 1.

Four other experiments were conducted in this manner, see Table III. Columns 2 and 3 in Table II state the catalyst and amount of water if any, respectively, added to the starting mixture, and column 4 states the molar ratio of water to sodium cyanide. The amount of catalyst added was 10%, calculated on 3-phenoxybenzaldehyde, in experiments 3 and 5. In experiment 5, 10.0 mmol instead of 10.5 mmol of 2-(4-chlorophenyl)-3-methylbutanoyl chloride was used.

TABLE II

| 1 | 2 | 3 | 4 | 5 | 6 |
|---|---|---|---|---|---|
| Exp. no. | Catalyst | Water added, ml | Molar ratio water to NaCN | Reaction time, h | Yield of ester, % |
| 1[1] | none | — | 0.012[3] | 3 | 19 |
| | | | | 20 | 18 |
| 2[1] | none | 0.02 | 0.105[3] | 3 | 38 |
| | | | | 24 | 98 |
| | | | | 44 | 99 |
| 3 | Dabanol 91-6[2] | 0.02 | 0.105[3] | 1 | 82 |
| | | | | 4 | 99 |
| 4[1] | none | 1.00 | 4.64 | 3 | 41 |
| | | | | 24 | 87 |
| | | | | 85 | 95 |
| 5 | Dobanol 91-6[2] | 1.00 | 4.64 | 6 | 83 |
| | | | | 20 | 88 |

[1] not according to the invention.
[2] for explanation of this word, see Table I.
[3] solid NaCN was present.

EXAMPLE III

Preparation of αcyano-3-phenoxybenzyl 2,2,3,3-tetramethyl-cyclopropanecarboxylate in the presence of n-heptane Methods A and B were applied to prepare the ester wanted.

Method A

A 50 ml round-bottomed flask equipped with a magnetic stirrer was charged with 10 mmol of 3-phenoxybenzaldehyde, 10 mmol of 2,2,3,3-tetramethylcyclopropanecarbonyl chloride, 12 mmol of sodium cyanide, 1.00 ml of water, a catalyst, if any, and 20 ml of n-heptane. The molar ratio of water to NaCN was 4.64, solid NaCN being absent. The catalyst was added in an amount of 0.20 mmol. The mixture thus formed was stirred for 1.5 hours and analysed.

Method B

The flask used for method A was charged with 10 mmol of 3-phenoxybenzaldehyde, 12 mmol of sodium cyanide, 10 ml of n-heptane, 1.00 ml of water and 0.20 mmol of a catalyst, if any, the molar ratio of water to NaCN being 4.64. An amount of 10 mmol of 2,2,3,3-tetramethylcyclopropanecarbonyl chloride dissolved in 10 ml of n-heptane was introduced into the flask during a period of 70–75 min. The yield of the ester was determined at the end of this period.

Two experiments were carried out in this manner. Table III states the catalysts used, if any. This Table also presents the yield of the desired ester.

TABLE III

| Exp. no. | Catalyst | Yield of ester, % | |
|---|---|---|---|
| | | Method A | Method B |
| 1[*] | none | 17 | 40 |
| 2 | Dobanol 91-6[**] | 44 | 98 |

[*] not according to the invention
[**] for explanation of this word, see Table I.

The amount of the catalysts used was 10% m in experiment 2, calculated on 3-phenoxybenzaldehyde.

EXAMPLE IV

Preparation of α-cyano-3-phenoxybenzyl 2-(4-chlorophenyl)-3-methylbutanoate on an enlarged scale Methods A (not according to the invention), and B were compared for the preparation of the ester wanted. Method A, in the absence of a phase transfer catalyst.

A 500 ml round-bottomed flask equipped with a paddle stirrer was charged with 100 mmol of 3-phenoxybenzaldehyde, 100 mmol of 2-(4-chlorophenyl)-3-methylbutanoyl chloride, 120 mmol of sodium cyanide, 10 ml of water (which dissolved all sodium cyanide) and 200 ml of n-heptane. After stirring for 45 hours the mixture was warmed to a temperature between 40° and 50° C and filtered. The filtrate was washed twice with 50 ml of a 1 M aqueous sodium bicarbonate solution, once with 50 ml of water, dried and the n-heptane was flashed from the dried solution to give the desired ester in a yield of 99% and a purity of 96%.

Method B, in the presence of a non-ionic surface-active agent.

The experiment described in Section A of this Example was repeated in the presence of 10%m of "Dobanol 91-6" (for explanation of this word, see Table I), calculated on 3-phenoxybenzaldehyde. After three hours' stirring the reaction mixture was warmed to a temperature between 40° and 50° C and filtered. An amount of 50 ml of ethanol was added (to break the emulsion formed) to the filtrate and the filtrate was washed twice with 50 ml of a 1 M aqueous solution of sodium bicarbonate, once with 50 ml of water, dried and the n-heptane was flashed from the dried solution to give the ester in a yield of 98% and a purity of 97%.

We claim:

1. A process for the preparation of an ester of formula I

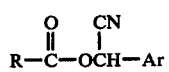
(I)

wherein Ar represents a phenoxy substituted phenyl group and R an alkyl group optionally substituted by halophenyl or alkylphenyl or a cyclopropyl group optionally substituted by alkyl, halogen, isobutenyl, dichlorovinyl or dibromovinyl, which process comprises contacting an aromatic aldehyde of the formula ArC(O)H and a (cyclo)aliphatic acyl halide of the formula RC(O)Hal, in which formulas Ar and R have the same meaning as in the formula I and Hal represents a halogen atom, with water, a water-soluble cyanide, a substantially water-immiscible aprotic solvent and a poly-(alkyleneoxy)-derivative containing from 1 to 50 alkyleneoxy units formed by reacting an alkanol containing 8 to 20 carbon atoms with ethylene oxide or propylene oxide as catalyst and recovering the desired ester product from the reaction mixture.

2. A process according to claim 1, in which the molar ratio of the amount of catalyst to the amount of aromatic aldehyde of the formula ArC(O)H is from 1:5 to 1:500.

3. A process according to claim 1, which is conducted at a temperature in the range of from 10° C to 50° C.

4. A process according to claim 1, in which the total amount of the water-soluble cyanide is dissolved in the water.

5. A process according to claim 4, in which the substantially water-immiscible aprotic solvent is a (cyclo)alkane or a mixture of (cyclo)alkanes.

6. A process according to claim 5, in which the alkane is n-heptane.

7. A process according to claim 5, in which the cycloalkane is cyclohexane.

8. A process according to claim 1, which is conducted in the presence of solid water-soluble cyanide.

9. A process according to claim 8, in which the substantially water-immiscible aprotic solvent is an aromatic hydrocarbon or a mixture of aromatic hydrocarbons.

10. A process according to claim 9, in which the aromatic hydrocarbon hydrocarbon is toluene.

11. A process according to claim 8, in which the substantially water-immiscible aprotic solvent is a chlorinated hydrocarbon.

12. A process according to claim 1, in which the starting molar ratio of the amount of water to the total amount of water-soluble cyanide is higher than 0.05.

13. A process according to claim 12, in which the starting molar ratio of the amount of water to the total amount of water-soluble cyanide is in the range of from 0.05 to 1.

14. A process according to claim 1, in which the molar ratio of the amount of (cyclo)aliphatic acyl halide of the formula RC(O)Hal to the amount of the aromatic aldehyde of the formula ArC(O)H is in the range of from 1.1 to 1.0.

15. A process according to claim 5, in which the molar ratio of the amount of (cyclo)aliphatic acyl halide of the formula RC(O)Hal to the amount of the aromatic aldehyde of the formula ArC(O)H is 1.0.

16. A process according to claim 1, in which the water-soluble cyanide is sodium cyanide.

17. A process according to claim 1, in which Hal in the formula RC(O)Hal represents a chlorine atom.

18. A process according to claim 1, in which the group R in the formula RC(O)Hal is optionally substituted (cyclo)alkyl group having a tertiary or quaternary carbon atom bound to the group —C(O)Hal.

19. A process according to claim 18, in which the group R is a 1-(4-chlorophenyl)-2-methylpropyl group or an isopropyl group.

20. A process according to claim 18, in which the group R is an optionally substituted cyclopropyl group.

21. A process according to claim 20, in which the group R is a 2,2,3,3-tetramethylcyclopropyl group.

22. A process according to claim 20, in which the group R is a 2-(2,2-dichlorovinyl)-3,3-dimethylcyclopropyl group.

23. A process according to claim 19, which is carried out by forming a mixture of the total amounts of the aromatic aldehyde, the (cyclo)aliphatic acyl halide, the water, the water-soluble cyanide and the substantially water-immiscible aprotic solvent, and stirring the mixture thus formed.

24. A process according to claim 20, which is carried out by gradual addition of the cycloaliphatic acyl halide to a stirred mixture of the aromatic aldehyde, the water, the water-soluble cyanide and the substantially water immiscible aprotic solvent.

25. A process according to claim 1 wherein the catalyst is an alcohol ethoxylate.

26. A process according to claim 25 wherein the water-soluble cyanide is sodium cyanide and the solvent is an alkane, a cycloalkane, an aromatic hydrocarbon, a chlorinated hydrocarbon or a mixture thereof.

27. A process according to claim 26 wherein the catalyst is an alcohol ethoxylated prepared using 5 to 9 moles of ethylene oxide per mole of alcohol or alcohol mixture.

28. A process according to claim 27 which is conducted at a temperature in the range of from 10° C to 50° C, with a molar ratio of the amount of (cyclo)aliphatic acyl halide to the amount of aromatic aldehyde is from 1.1 to 1.0 and in which the starting molar ratio of the amount of water to the total amount of water-soluble cyanide is higher than 0.05.

29. A process according to claim 28 wherein the catalyst is formed from a $C_9$–$C_{11}$ alcohol mixture and contains an average of 6 ethyleneoxy units.

30. A process according to claim 29 wherein the ester of formula I is α-cyano-3-phenoxybenzyl 2-(4-chlorophenyl)-3-methyl-butanoate.

* * * * *